United States Patent [19]

Connolly et al.

[11] Patent Number: 5,324,715
[45] Date of Patent: Jun. 28, 1994

[54] PROTEIN FOR INHIBITING COLLAGEN-STIMULATED PLATELET AGGREGATION

[75] Inventors: Thomas M. Connolly, Harleysville; Paul M. Keller, Lansdale, both of Pa.

[73] Assignee: Merck & Co., Inc., Rahway, N.J.

[21] Appl. No.: 44,547

[22] Filed: Apr. 7, 1993

Related U.S. Application Data

[63] Continuation of Ser. No. 594,917, Oct. 9, 1990, abandoned.

[51] Int. Cl.$^5$ .............................................. A61K 37/00
[52] U.S. Cl. .................................... 514/12; 530/855; 530/350; 424/550
[58] Field of Search ....................... 530/350, 853, 913; 514/12; 424/550

[56] References Cited

U.S. PATENT DOCUMENTS 4,832,849  5/1989  Cardin et al. ........................ 210/635

FOREIGN PATENT DOCUMENTS 0263608  11/1990  European Pat. Off. .
87/00860  11/1990  World Int. Prop. O. .

OTHER PUBLICATIONS

Gasic et al., Proc. Am. Assoc. Cancer Res., 27:66 Abstract #261 (1987).
Gasic et al., Cancer Res. 43 pp. 1633-1636 (1983).
Gasic et al., Cancer Res. 44 pp. 5670-5676 (1984).
Tuszynski et al., J. Biol. Chem. 262(20) pp. 9718-9723 (1987).
Han, et al. Gene 75 pp. 47-57 (1989).
Baskova et al. Chem. Abs. 107 No. 23 p. 33 (1987).
Thacker, 69 USPQ 126 (1946).

*Primary Examiner*—Robert A. Wax
*Assistant Examiner*—David B. Schmickel
*Attorney, Agent, or Firm*—Richard S. Parr; Melvin Winokur; Paul D. Matukaitis

[57] ABSTRACT

A protein isolated from crude *Haementeria officinalis* extract which blocks stimulation of platelet aggregation by collagen. The protein has a molecular weight of approximately 16,000. A method of isolating the protein and using the protein to prevent or delay blood coagulation by blocking the stimulation of platelet aggregation by collagen is also described. The protein is useful in the prevention, prophylaxis, therapy and treatment of thrombotic diseases.

7 Claims, 2 Drawing Sheets

CUT BLUE BLUESCRIPT SK (STRATAGENE) WITH Not1 AND Sal1

↓

LIGATE INSERT INTO BLUESCRIPT VECTOR

↓

↓

SEQUENCE INSERT

↓

PCR AMPLIFY MATURE ORF WITH OLIGONUCLEOTIDE PRIMERS:
ATA TGG ATC CTG TCT TTG GAT AAA AGA CAG GAT GAA GAT
GCC GGT GGT (5' PRIMER),
ATA TCG GGA TCC TAT TTT GAA CAA GCG TGA AGG (3' PRIMER)

↓

CUT PCR PRODUCT WITH Bam H1, GEL PURIFY

↓

LIGATE Bam H1 CUT PCR PRODUCT WITH pKH4α2

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 147 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:1:

```
Met Asn Ser Phe Leu Phe Ser Leu Ala Cys Ser Leu Leu Val Ala Ile
1               5                   10                  15

Pro Ala Ile Arg Ala Gln Asp Glu Asp Ala Gly Gly Ala Gly Asp Glu
        20                  25                  30

Thr Ser Glu Gly Glu Asp Thr Thr Gly Ser Asp Glu Thr Pro Ser Thr
35                      40                  45

Gly Gly Gly Gly Asp Gly Gly Asn Glu Glu Thr Ile Thr Ala Gly Asn
50                  55                  60

Gly Asp Cys Trp Ser Lys Arg Pro Gly Trp Lys Leu Pro Asp Asn Leu
65                  70                  75                  80

Leu Thr Lys Thr Glu Phe Thr Ser Val Asp Glu Cys Arg Lys Met Cys
85                  90                  95

Glu Glu Ser Ala Val Glu Pro Ser Cys Tyr Ile Leu Gln Ile Asn Thr
100                 105                 110

Glu Thr Asn Glu Cys Tyr Arg Asn Asn Glu Gly Asp Val Thr Trp Ser
115                 120                 125

Ser Leu Gln Tyr Asp Gln Pro Asn Val Val Gln Trp His Leu His Ala
130                 135                 140

Cys Ser Lys
145
```

( 2 ) INFORMATION FOR SEQ ID NO:2:

( i ) SEQUENCE CHARACTERISTICS:
        ( A ) LENGTH: 441 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

| | | | | | |
|---|---|---|---|---|---|
| ATGAACTCAT | TCCTGTTCTC | ACTCGCCTGC | TCTTTGCTGG | TTGCCATCCC | AGCTATCAGG | 60 |
| GCCCAGGATG | AAGATGCCGG | TGGTGCCGGA | GATGAAACCA | GTGAAGGCGA | AGACACTACT | 120 |
| GGAAGTGATG | AAACACCCTC | AACAGGAGGA | GGAGGCGATG | GTGGAAATGA | AGAAACCATA | 180 |
| ACTGCTGGCA | ATGGAGATTG | CTGGTCTAAA | CGGCCTGGCT | GGAAGCTGCC | TGACAATCTG | 240 |
| TTGACGAAGA | CTGAATTCAC | CAGCGTCGAT | GAATGCAGAA | AGATGTGCGA | AGAATCTGCC | 300 |
| GTGGAACCAT | CCTGCTACAT | TCTGCAAATC | AACACAGAAA | CCAACGAATG | CTATAGAAAT | 360 |
| AACGAAGGTG | ATGTCACGTG | GTCAAGTTTA | CAATATGATC | AACCAAATGT | TGTTCAATGG | 420 |
| CACCTTCACG | CTTGTTCAAA | A | | | | 441 |

( 2 ) INFORMATION FOR SEQ ID NO:3:

( i ) SEQUENCE CHARACTERISTICS:
        ( A ) LENGTH: 126 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:3:

```
    Gln Asp Glu Asp Ala Gly Gly Ala Gly Asp Glu Thr Ser Glu Gly Glu
    1               5                   10                  15

Asp Thr Thr Gly Ser Asp Glu Thr Pro Ser Thr Gly Gly Gly Gly Asp
20                  25                  30

Gly Gly Asn Glu Glu Thr Ile Thr Ala Gly Asn Gly Asp Cys Trp Ser
    35                  40                  45

Lys Arg Pro Gly Trp Lys Leu Pro Asp Asn Leu Leu Thr Lys Thr Glu
50                  55                  60

Phe Thr Ser Val Asp Glu Cys Arg Lys Met Cys Glu Glu Ser Ala Val
    65                  70                  75                  80

Glu Pro Ser Cys Tyr Ile Leu Gln Ile Asn Thr Glu Thr Asn Glu Cys
    85                  90                  95

Tyr Arg Asn Asn Glu Gly Asp Val Thr Trp Ser Ser Leu Gln Tyr Asp
    100                 105                 110

Gln Pro Asn Val Val Gln Trp His Leu His Ala Cys Ser Lys
    115                 120                 125
```

( 2 ) INFORMATION FOR SEQ ID NO:4:

( i ) SEQUENCE CHARACTERISTICS:
        ( A ) LENGTH: 378 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

| | | | | | |
|---|---|---|---|---|---|
| CAGGATGAAG | ATGCCGGTGG | TGCCGGAGAT | GAAACCAGTG | AAGGCGAAGA | CACTACTGGA | 60 |
| AGTGATGAAA | CACCCTCAAC | AGGAGGAGGA | GGCGATGGTG | GAAATGAAGA | AACCATAACT | 120 |
| GCTGGCAATG | GAGATTGCTG | GTCTAAACGG | CCTGGCTGGA | AGCTGCCTGA | CAATCTGTTG | 180 |
| ACGAAGACTG | AATTCACCAG | CGTCGATGAA | TGCAGAAAGA | TGTGCGAAGA | ATCTGCCGTG | 240 |
| GAACCATCCT | GCTACATTCT | GCAAATCAAC | ACAGAAACCA | ACGAATGCTA | TAGAAATAAC | 300 |
| GAAGGTGATG | TCACGTGGTC | AAGTTTACAA | TATGATCAAC | CAAATGTTGT | TCAATGGCAC | 360 |
| CTTCACGCTT | GTTCAAAA | | | | | 378 |

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:5:

ATTCGTCGAC AATACGACTC ACTA 24

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:6:

ACGTTAGGTT GGTCGTATTG 20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:7:

ACGTTCGGTT GGTCGTATTG 20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:8:

ACATTGGGCT GATCATACTG 20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:9:

ACGTTTGGTT GGTCGTATTG 20

( 2 ) INFORMATION FOR SEQ ID NO:10:

( i ) SEQUENCE CHARACTERISTICS:
        ( A ) LENGTH: 7 amino acids
        ( B ) TYPE: amino acid -continued

```
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:10:

Gln  Tyr  Asp  Gln  Pro  Asn  Val
    1                 5

( 2 ) INFORMATION FOR SEQ ID NO:11:

( i ) SEQUENCE CHARACTERISTICS:
        ( A ) LENGTH: 48 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:11:

ATATGGATCC  TGTCTTTGGA  TAAAAGACAG  GATGAAGATG  CCGGTGGT              48

( 2 ) INFORMATION FOR SEQ ID NO:12:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:12:

ATATCGGGAT  CCTATTTTGA  ACAAGCGTGA  AGG                                33
```

PROTEIN FOR INHIBITING COLLAGEN-STIMULATED PLATELET AGGREGATION

This is a continuation of application Ser. No. 07/594,917 filed on Oct. 9, 1990, now abandoned.

BACKGROUND OF THE INVENTION

Normal hemostasis in man is governed by a complex series of interrelated mechanisms involving both cellular and humoral biochemical components. The biochemical pathway involves injury to intact endothelial cells, stimulation of platelets and activation of coagulation mechanisms. When a vessel is damaged and the subendothelium is exposed, platelets very rapidly adhere to some of the constituents of the vessel wall, notably collagen. Although platelets also adhere to other subendothelial constituents, only collagen has been reported to stimulate platelets to release their granule contents and recruit other platelets to the injury site.

SUMMARY OF THE INVENTION

The invention comprises a protein (LAPP) isolated from crude *Haementeria officinalis* extract which blocks stimulation of platelet aggregation by collagen, and which blocks platelet adhesion to collagen. The protein has a molecular weight of approximately 16,000. The invention also comprises methods of preparing the protein, such as by purifying the protein from *Haementeria officinalis* salivary gland extract, and a method of using the protein to prevent or delay blood coagulation by blocking the stimulation of platelet aggregation by collagen. The protein is useful in the prevention, prophylaxis, therapy and treatment of thrombotic diseases.

DETAILED DESCRIPTION OF THE INVENTION

Figure 1:
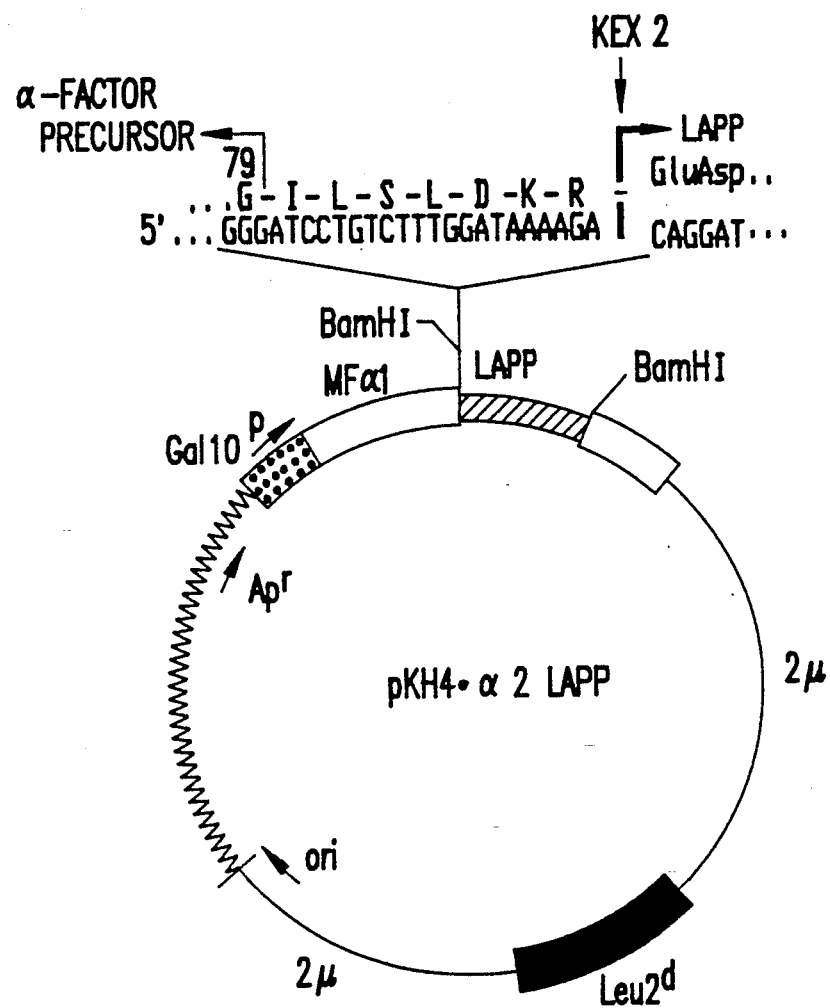
FIG. 1 shows the yeast vector used for expression of the r-LAPP synthetic gene sequence.

The invention encompasses the protein isolated from *Haementeria officinalis* and homologs, isoforms or genetic variants, provided that each one blocks stimulation of platelet aggregation by collagen and reacts with antibodies specific for the specified protein.

Proteins

Proteins of the invention include variations on the disclosed purified protein sequences which conserve the activity of the disclosed sequences, including fragments or subunits, naturally occurring mutations, allelic variants, randomly generated artificial mutants and intentional sequence variation which conserves activity. Fragments or subunits refers to any portion of the sequence which contains fewer amino acids than the complete protein, e.g. partial sequences excluding portions at the N- and/or C-termini of the complete protein.

Proteins of the invention also include disclosed recombinant protein sequences which conserve the activity of the purified protein sequences. Also included are hybrid proteins, such as fusion proteins or proteins resulting from the expression of multiple genes within the expression vector, and may include a polypeptide having the specific activity of a disclosed protein linked by peptide bonds to a second polypeptide.

It will be understood that other variants of the proteins of the present invention are included, especially any variants that differ from the isolated protein only by conservative amino acid substitution. Such conservative amino acid substitutions are defined as "sets" in Table I of Taylor, *J. Mol. Biol.*, 188, 233 (1986).

The protein of the present invention may be prepared by synthetic means or by recombinant techniques, or may be obtained from crude *Haementeria officinalis* extract as described below.

IDENTIFICATION OF INHIBITION OF COLLAGEN-STIMULATED Platelet Aggregation

Human platelets are washed in modified Tyrode's buffer with no Ca++ with 0.2 mg/ml fibrinogen. The washed platelets are incubated at 37° C. for 2 minutes with the sample to be tested. Collagen at 1 or 2 μg/ml final concentration is added and platelet aggregation in an aggregometer is monitored. Inhibitory activity is defined as a decrease in the rate and/or extent of platelet aggregation.

IDENTIFICATION OF BLOCKING OF PLATELET ADHESION TO Collagen

Recombinant, yeast-expressed LAPP was shown to block the adhesion of washed platelets to Collagen-coated microliter plates.

Polystyrene 96-well microtiter plates (Costar, Cambridge, Mass.) are coated with 100 μl per well of 40 μg/ml collagen dissolved in 5 mM acetic acid for 1 hour at room temperature followed by blocking of the non-specific cell binding sites by addition of 200 μl of 10 mg/ml heat-denatured BSA for 1 hour. Control wells are coated with BSA only. The wells are rinsed three times with HEPES buffered saline (HBS) containing 20 mM HEPES, pH 7.4, 0.14M NaCl, and 2 mM MgCl$_2$. 100 μl of washed platelets are incubated with various concentrations of LAPP or buffer as a control for 5 min at room temperature and then added to each collagen coated well and incubated at room temperature for 45 min., nonadherent platelets are removed by aspiration, and the wells are rinsed three times with 200 μl of HBS. The number of adhered platelets is determined by protein assay, using the BCA reagent and measuring the absorbance of each well at 562 nM.

EXAMPLE 1

Isolation of Collagen-stimulated Platelet Aggregation Inhibitor From *Haementeria officialis* Extract

*Haementeria officinalis* leeches were dissected and the salivary gland tissue processed through crude extract which was prepared in 20 mM HEPES, pH 7.8, 10 mM CaCl$_2$. This extract was passed over a Heparin agarose column equilibrated in the same buffer and then washed with the same buffer.

The antagonist of collagen-mediated platelet aggregation was found in the 0.1, 0.2 and 0.3M NaCl Heparin agarose eluates. The 0.1, 0.2 or 0.3M samples were concentrated on the Centricon-10 microconcentrator, followed by Superose 12 10/30 gel filtration. An elution buffer of 0.15M NaCl in 0.05M NaPO$_4$, pH 7.2, was used in an effort to maintain biological activity. Examination of the Superose 12 column fractions for antagonism of collagen-mediated platelet aggregation isolated the activity to the peak eluting at 34.73 minutes. The isolate was then purifed on reverse phase C$_{18}$ HPLC.

Amino acid composition analysis of the isolated protein showed the following:

| Amino Acid | Residue/mole |
| --- | --- |
| Asp | 12.5 |
| Thr | 14 |
| Ser | 14 |
| Glu | 14 |
| Gly | 20 |
| Ala | 8 |
| Cys | 12 |
| Val | 6 |
| Iso | 4.5 |
| Leu | 9.5 |
| Tyr | 4.5 |
| Phe | 3 |
| His | 2 |
| Lys | 5 |
| Arg | 5 |
| Pro | 5 |

EXAMPLE 2

Isolation of Collagen-stimulated Platelet Aggregation Inhibitor From *Haementeria officinalis* Extract

*Haementeria officinalis* leeches were dissected and the salivary gland tissue processed through crude extract which was prepared in 20 mM HEPES, pH 7.8, 10 mM CaCl$_2$. Purification procedure was similar to the procedure described in Example 1 except as further described. The protein was eluted with 0.35 NaCl in 20 mM Tris-HCl, pH 8.7, rather than 0.15 NaCl in 0.05M NaPO$_4$, pH 7.2. The protein was concentrated and desalted on a Centricon-10 microconcentrator and then either applied to a Superose 12 column as in Example 1 or filtered through a Centricon-30 filter. The samples were dried, resuspended in H$_2$O, and applied to a C$_{18}$ reverse phase HPLC for final purification.

Amino acid composition analysis of the isolated protein showed the following:

| Amino Acid | Residue/mole |
| --- | --- |
| Asp | 12.4 |
| Thr | 10.6 |
| Ser | 10.3 |
| Glu | 10 |
| Gly | 21 |
| Ala | 5 |
| Cys | 1.4 |
| Val | 3.1 |
| Iso | 1.9 |
| Leu | 5 |
| Tyr | 3.3 |
| Phe | 1 |
| His | 6.4 |
| Lys | 4.5 |
| Arg | 2.9 |
| Pro | 4.5 |

Peptides were generated by V8 or Lys C protease digestion of the purified protein followed by their isolation on C$_{18}$ reverse phase HPLC chromatography and sequencing. The following peptide sequence were obtained:

---

Peptide 1

Thr Ile Thr Ala Gly Asn Gly Asp Cys Trp Ser Lys Arg Pro Gly Trp Lys Leu Pro Asp Asn Leu Leu Thr Lys Thr Glu Phe Thr Ser Val Asp Glu

Peptide 2

Thr Glu Phe Thr Ser Val Asp Glu Cys Arg Lys

Peptide 3

Ile Leu Gln Ile Asn

Peptide 4

Gly Asp Val Thr Trp Ser Ser Leu Gln Tyr Asp Gln Pro Asn Val Val Gln Trp His Leu

Peptide 5

Ser Leu Gln Tyr Asp Gln Pro Asn Val Val Gln Trp His Leu His Ala Cys

---

EXAMPLE 3

In vitro Activity of the *Haementeria officinalis* Collagen-stimulated Platelet Aggregation Inhibitor Our studies show that while platelet aggregation is stimulated by 2 μg/ml collagen, addition of the collagen-stimulated platelet aggregation inhibitor isolated in Examples 1 and 2 inhibits such stimulation. The IC$_{50}$ for this inhibition was 45 nM. Inhibition of collagen stimulation was overcome by later addition of 0.25 mM arachidonic acid.

Recombinant DNA Technology

Recombinant DNA technology may be used to produce proteins of the invention. This technology allows segments of genetic information, DNA, from different cells, and usually from different organisms, to be joined end-to-end outside the organisms from which the DNA was obtained and to incorporate this hybrid DNA into a cell that will allow the production of the protein for which the original DNA encodes. Genetic information, DNA or mRNA, is isolated and incorporated into an appropriate cloning vector, and transduced into an appropriate host cell.

Cloning vectors useful for this technology include a DNA sequence which accommodates specific experimental foreign DNA. The vectors are introduced into host cells that can exist in a stable manner and express the protein dictated by the experimental DNA. Cloning vectors may include plasmids, bacteriophage, viruses and cosmids.

Expression vectors are DNA sequences that are required for the transcription of cloned copies of genes and the translation of their mRNAs in an appropriate host. These vectors can express either procaryotic or eucaryotic genes in a variety of cells such as bacteria, yeast, insect and mammalian cells. Proteins may also be expressed in a number of virus systems. A suitably constructed expression vector contains an origin of replication for autonomous replication in host cells, selective markers, a limited number of useful restriction enzyme sites, a high copy number, and strong promoters. Promoters are DNA sequences that direct RNA polymerase to bind to DNA and initiate RNA synthesis; strong promoters cause such initiation at high frequency. Expression vectors may include, but are not limited to cloning vectors, modified cloning vectors and specifically designed plasmids or viruses.

Expression Systems

Procaryotes most frequently are represented by various strains of *E. coli*. Other microbial strains may be used, such as bacilli, e.g. *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., *Gene* (1977) 2:95. Commonly used procaryotic control sequences, which are defined herein to include promoters for transcription initiation, optionally with an operator, along with ribosome binding site sequences, include such commonly used promoters as the beta-lactamase (penicillinase) and lactose (lac) promoter systems (Chang et al., *Nature* (1977) 198:1056) and the tryptophan (Trp) promoter system (Goeddel et al., *Nucleic Acids Res.* (1980) 8:4057) and the lambda-derived $P_L$ promoter and N-gene ribosome binding site (Shimatake et al., *Nature* (1981) 292:128). However, any available promoter system compatible with procaryotes can be used.

Expression systems useful in the eucaryotic systems of the invention comprise promoters derived from appropriate eucaryotic genes. A class of promoters useful in yeast, for example, include promoters for synthesis of glycolytic enzymes, including those for 3-phosphoglycerate kinase (Hitzeman et al., *J. Biol. Chem.* (1980) 255:2073). Other promoters include those from the enolase gene (Holland, M. J., et al., *J. Biol. Chem.* (1981) 256:1385) or the Leu2 gene obtained from YEp13 (Broach, J., et al., *Gene* (1978) 8:121).

The preferred expression system for preparing recombinant LAPP is described in Example 4. The system uses yeast strain *Saccharomyces cerevisiae* BJ1995.

Suitable mammalian promoters including the early and late promoters from SV40 (Fiers, et al., *Nature* (1978) 273:113) or other viral promoters such as those derived from polyoma, adenovirus II, bovine papilloma virus or avian sarcoma viruses. Suitable viral and mammalian enhancers are cited above. In the event plant cells are used as an expression system, the nopaline synthesis promoter is appropriate (Depicker, A. et al., *J. Mol. Appl. Gen.* (1982) 1:561).

Insect cell expression systems useful for expressing the proteins include the modified versions of the system described in Smith et al., U.S. Pat. No. 4,745,051. Baculovirus DNA comprising a baculovirus gene or a portion thereof which includes a promoter of the baculovirus gene is cleaved to obtain a DNA fragment containing at least the promoter. The desired product protein is prepared by infecting a susceptible host insect cell with a recombinant baculovirus expression vector wherein the expression vector is a recombinant baculovirus genome comprising at least one selected heterologous product protein polypeptide structural gene under the transcriptional control of a baculovirus polyhedrin promoter.

The recombinant baculovirus expression vector capable of expressing a selected gene in a host insect cell is preferably produced by cleaving baculovirus DNA to produce a DNA fragment comprising a baculovirus polyhedrin promoter, and sufficient flanking DNA sequences to facilitate homologous recombination; inserting the baculovirus DNA fragment into a cloning vehicle to form a modified cloning vector; identifying a selected restriction site of the cloned baculovirus DNA fragment which is under the transcriptional control of the baculovirus polyhedrin promoter; deleting from the modified cloning vector the additional restriction site in the baculovirus DNA fragment under the transcriptional control of the baculovirus polyhedrin promoter; inserting a selected heterologous gene into the unique restriction site to form a recombinant shuttle vector; contacting the baculovirus DNA so as to effect recombination, thereby producing a mixture of recombinant and nonrecombinant baculoviruses; and isolating a recombinant baculovirus expression vector from the mixture.

VECTOR CONSTRUCTION

Figure 2:
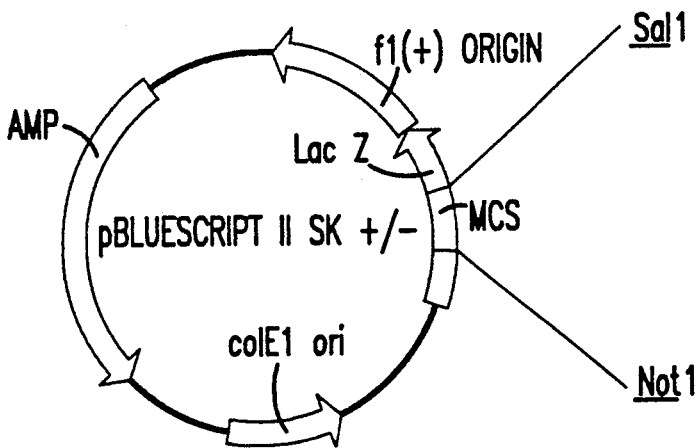
FIG. 2 shows a flow diagram of the preparation of the LAPP clone.
Figure 2:
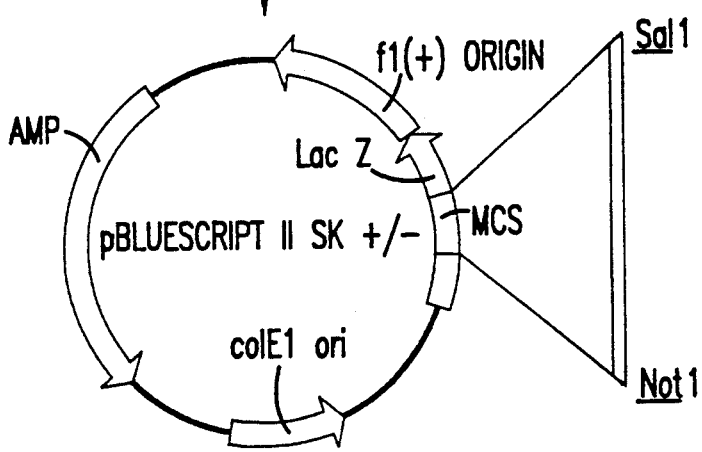

The expression vector preferred for preparing recombinant LAPP in yeast, is described in Example 4 and FIGS. 1 and 2.

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g. New England Biolabs, Product Catalog. In general, about 1 $\mu$g of plasmid or DNA sequence is cleaved by one unit of enzyme in about 20 $\mu$l of buffer solution. Typically, an excess of restriction enzyme is used to ensure complete digestion of the DNA substrate. Incubation times of about 1 to 2 hours at about 37° C. are workable, although variations can be tolerated. After each incubation, the digestion product is exposed to phenol/chloroform extraction and may be followed by running over a Sephadex ® G-50 spin column. If desired, size separation of the cleaved fragments may be performed by polyacrylamide gel or agarose gel electrophoresis using standard techniques. A general description of size separations is formed in *Methods in Enzymology* (1980)65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20° to 25° C. in 50 mM Tris, pH 7.6, 50 mM NaCl, 6 mM MgCl$_2$, 6 mM DTT and 5-10 $\mu$MdNTPs. The Klenow fragment fills in 5' overhangs but removes protruding 3' single strands, even in the process of the four dNTPs. If desired, selective repair can be performed by supplying selected dNTPs within the limitations dictated by the nature of the sticky ends. After treatment with Klenow, the mixture is extracted with phenol/chloroform and ethanol precipitated followed by running over a Sephadex ® G-50 spin column. Treatment under appropriate conditions with S1 nuclease results in hydrolysis of any single-stranded portion.

As mentioned above, oligonucleotides may be prepared by the triester method of Matteucci, et al. (*J. Am. Chem. Soc.* (1981) 103:3185) or using commercially available automated oligonucleotide synthesizers. Kinasing of single strands prior to annealing or for labelling is achieved using an excess, e.g., approximately 10 units of polynucleotide kinase to 0.1 nmole substrate in the presence of 50 mM Tris, pH 7.6, 10 mM MgCl$_2$, 5 mM dithiothreitol, 1-2 mM ATP, 1.7 pmoles $^{32}$P-ATP (2.9 mCi/mmole), 0.1 mM spermidine, 0.1 mM EDTA.

Ligations are performed in 15-30 μl volumes under the following standard conditions and temperatures: 20 mM Tris-HCl, pH 7.5, 10 mM MgCl$_2$, 10 mM DTT, 33 μg/ml BSA, 10 mM-50 mM NaCl, and 1 mM ATP, 0.3-0.6 (Weiss) units T4 DNA ligase at 14° C. (for "blunt end" ligation). Intermolecular "sticky end" ligations are usually performed at 33-100 μg/ml total DNA concentrations (5-100 nM total end concentration). Intermolecular blunt end ligations (usually employing a 10-30 fold molar excess of linkers) are performed at 1 μM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{2+}$ using about 1 unit of BAP per μg of vector at 60° C. for about 1 hour. In order to recover the nucleic acid fragments, the preparation is extracted with phenol/chloroform and ethanol precipitated and desalted by application to a Sephadex ® G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis is used. This is conducted using a primer synthetic oligonucleotide complementary to a single stranded plasmid or phage DNA to be mutagenized except for limited mismatching, representing the desired mutation. Briefly, the synthetic oligonucleotide is used as a primer to direct sythesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

PROBING cDNA LIBRARIES cDNA or genomic libraries are screened using the colony or plaque hybridization procedure. Each plate containing bacterial colonies (or recombinant phage-infected bacteria) is replicated onto duplicate nitrocellulose filter papers (S & S type BA-85) and, for bacterial colony screens, the colonies are allowed to grow at 37° C. for 14-16 hours on L agar containing 50 μg/ml Amp. The bacteria are lysed, plasmid or phage and DNA fixed to the filter by sequential treatment for 5 minutes each with 0.2N NaOH, 1.5M NaCl, then 0.5M Tris pH 7.5, 1.5M NaCl and then 2×standard saline citrate (2×SSC). Filters are air dried and baked at 80° C. for 2 hours. The duplicate filters are prehybridized at 42° C. for 6-8 hours with 10 ml per filter of DNA hybridization buffer (5×SSC, pH 7.0, 5×Denhardt's solution (polyvinyl pyrrolidine, plus Ficoll and bovine serum albumin; 1×=0.02% of each), 50 mM sodium phosphate buffer at pH 7.0, 0.2% SDS, 20 μg/ml polyU, and 50 μg/ml denatured salmon sperm DNA.

The samples are hybridized with kinased probe under conditions which depend on the stringency desired. Typical moderately stringent conditions employ a temperature of 42° C. for 24-36 hours with 1-5 ml/filter of DNA hybridization buffer containing probe. For higher stringencies, high temperatures and shorter times are employed. The filters are washed four times for 30 minutes each time at 37° C. with 2×SSC, 0.2% SDS and 50 mM sodium phosphate buffer at pH 7, then are washed twice with 2×SSC and 0.2% SDS, air dried and are autoradiographed at −70° C. for 2 to 3 days.

OLIGONUCLEOTIDE PRIMERS

Oligonucleotide primers are prepared which will hybridize to different strands of the desired sequence and at relative positions along the sequence such that an extension product synthesized from one primer, when it is separated from its template (complement), can serve as a template for extension of the other primer into a nucleic acid of defined length. The primers may be prepared using any suitable method, such as, for example, the phosphotriester and phosphodiester methods, described respectively in Narang, S.A., et al. *Meth. Enzymol.*, 68, 90 (1979) and Brown, E.L. et al., *Meth. Enzymol*, 68, 109 (1979), or automated embodiments thereof. In one such automated embodiment, diethylphosphoramidites are used as starting materials and may be synthesized as described by Beaucage et al., *Tetrahedron Letters* (1981), 22: 1859-1862. One method for synthesizing oligonucleotides on a modified solid support is described in U.S. Pat. No. 4,458,066. It is also possible to use a primer which has been isolated from a biological source (such as a restriction endonuclease digest).

POLYMERASE CHAIN REACTION AMPLIFICATION

Large amounts of DNA coding for the protein may be obtained using polymerase chain reaction (PCR) amplification techniques as described in Mullis et al., U.S. Pat. No. 4,800,159. The extension product of one primer, when hybridized to another primer, becomes a template for the production of the nucleic acid sequence.

The primer template complexes act as substrate for DNA polymerase which, in performing its replication function, extends the primers. The region in common with both primer extensions, upon denaturation, serves as template for a repeated primer extension.

Taq DNA Polymerase catalyzes primer extension in the amplification process. The enzyme is a thermostable DNA polymerase isolated from *Thermus aquaticus*. Because it stays active through repeated elevations to high denaturation temperatures, it needs to be added only once. Deoxynucleotide triphosphates provide the building blocks for primer extension.

The nucleic acid sequence strands are heated until they separate, in the presence of oligonucleotide primers that bind to their complementary strand at a particular site of the template. This process is continued with a series of heating and cooling cycles, heating to separate strands, and cooling to reanneal and extend the sequences. More and more copies of the strands are generated as the cycle is repeated. Through amplification, the coding domain and any additional primer-encoded information such as restriction sites or translation signals (signal sequences, start condons and/or stop codons) is obtained. PCR protocols are often performed at the 100 µL scale in 0.5-mL microcentrifuge tubes. The PCR sample may be single- or double-stranded DNA or RNA. If the starting material is RNA, reverse transcriptase is used to prepare first strand cDNA prior to PCR. Typically, nanogram amounts of cloned template, up to microgram amounts of genomic DNA, or 20,000 target copies are chosen to start optimization trials.

PCR primers are oligonucleotides, typically 15 to 30 bases long, and are complementary to sequences defining the 5' ends of the complementary template strands. Non-template complementary 5' extensions may be added to primers to allow a variety of useful post amplification operations on the PCR product without significant perturbation of the amplification itself. It is important that the two PCR primers not contain more than two bases complementary with each other, especially at their 3' ends. Internal secondary structure should be avoided in primers.

Because Taq DNA Polymerase has activity in the 37°–55° C. range, primer extension will occur during the annealing step and the hybrid will be stabilized. The concentrations of the primers are preferably equal in conventional PCR and, typically, within 0.1-to 1-µM range.

In the standard PCR protocol, each deoxynucleotide triphosphate concentration is preferably about 200 µM. The four dNTP concentrations are preferably above the estimated Km of each dNTP (10–15 µM).

Preferably, PCR buffer is composed of about 500 mM potassium chloride, 100 mM Tris-HCl (pH 8.3 at room temperature), 15 mM magnesium chloride, and 0.01% w/v gelatin. In the presence of 0.8 mM total dNTP concentration, a titration series in small increments over the 1.5-to 4-mM range will locate the magnesium concentration producing the highest yield of a specific product. Too little free magnesium will result in no PCR product and too much free magnesium may produce a variety of unwanted products.

Preferably, in a 100-µL reaction volume, 2.0 to 2.5 units of Taq DNA Polymerase are recommended. The enzyme can be added conveniently to a fresh master mix prepared for a number of reactions, thereby avoiding accuracy problems associated with adding individual 0.5-µL enzyme aliquots to each tube. A typical PCR protocol for amplification of the DNA template includes a 1 minute 94° C. denaturation step, a 1 minute 37° C. primer annealing step, and a 2 minute 72° C. primer extension step. This will amplify a 500 base-pair product at least 100,000-fold in 25 cycles.

During DNA denaturation, sufficient time must be allowed for thermal equilibration of the sample. The practical range of effective denaturation temperatures for most samples is 92°–95° C., with 94° C. being the standard choice.

Primer annealing is usually performed first at 37° C., and the specificity of the product is evaluated. If unwanted bands are observed, the annealing temperature should be raised in subsequent optimization runs. While the primer annealing temperature range is often 37°–55° C., it may be raised as high as the extension temperature in some cases. Merging of the primer annealing and primer extension steps results in a two-step PCR process.

Primer extension, in most applications, occurs effectively at a temperature of 72° C. and seldom needs optimization. In the two-temperature PCR process the temperature range may be 65°–70° C. In situations where enzyme concentration limits amplification in late cycles, the extension is preferably increased linearly with cyclic number. Usually, 25 to 45 cycles are required for extensive amplification (i.e., 1,000,000 fold) of a specific target.

TRANSFORMATION

Depending on the host cell used, transformation is done using standard techniques appropriate to such cells. The calcium treatment employing calcium chloride, as described by Cohen, S. N., *Proc. Natl. Acad. Sci. USA* (1972) 69:2110, or the RbCl method described in Maniatis et al., *Molecular Cloning: A Laboratory Manual* (1982) Cold Spring Harbor Press, p. 254 is used for procaryotes or other cells which contain substantial cell wall barriers. Infection with *Agrobacterium tumefaciens* (Shaw, C. H., et al., *Gene* (1983) 23:315) is used for certain plant cells. For mammalian cells without such cell walls, the calcium phosphate precipitation method of Graham and van der Eb, *Virology* (1978) 52:546 is preferred. Transformations into yeast are carried out according to the method of Van Solingen, P., et al., *J. Bacter.* (1977) 130:946 and Hsiao, C. L. et al., *Proc. Natl. Acad. Sci. USA* (1979) 76:3829.

Example 4 describes a preferred yeast expression system for preparing recombinant LAPP.

EXAMPLE 4

Identification of Nucleic Acid Sequence and Entire Amino Acid Sequence and Expression of 147 Amino Acid Leech Antiplatelet Protein (LAPP) in Transformed *Saccharomyces cerevisiae* BJ1995

Isolate Total DNA From
Leech λ GT22 Library

PCR amplify library using
λgt22 arm primer
ATT CGT CGA CAA TAC GAC TCA CTA
and a degenerate oligonucleotide
based on peptide sequence
          A
AC GTT CGG TTG GTC GTA TTG
  A    G     C    A    A    C
          T
Sequence to confirm PCR
product is derived from leech
anti-platelet protein.

-continued
Radiolabel PCR product,
use to screen Leech λgt-22
Library. Plaque purify
positive clones.

↓

Isolate phage DNA, cut
with Not 1 and Sal 1, gel purify
isolate approx. 700 base pair
insert containing gene.

↓

Not 1 ═══════ Sal 1

Total leech salivary gland RNA was obtained from dissected salivary glands of *Haementeria officinalis* by the method of Han, J. et al., Biochemistry 26, 1617 (1987). Poly A+ RNA was isolated according to Maniatis, T. et al., Molecular Cloning: A Laboratory Manual, Cold Spring Harbor Laboratory, Cold Spring Harbor, N.Y. 1982.

From the isolated poly A+ RNA, a λgt22 expression-cDNA library was constructed according to Han, J. et al., Nucleic Acids Research 15, 6304 (1987). Two bacteriophage RNA polymerase promoters, SP6 and T7, were introduced into double-stranded cDNA and cloned into SalI and NotI sites of λgt22 in one orientation. About $2 \times 10^6$ primary independent cDNA clones were obtained.

Screening of the λgt22 library was performed using a polymerase chain reaction (PCR) generated probe. This probe was made by PCR amplifying total DNA isolated from the λgt22 library using an oligonucleotide primer which binds to one arm of the λgt22 (at the 5' end of the inserted cDNA) and a second degerate oligonucleotide primer based on the sequence of a peptide from a V8 digest of the 16,000 molecular weight leech antiplatelet protein.

The sequence of the oligonucleotide which binds to the arm of the λgt22 is Sequence ID No. 5. The sequences of the degenerate oligonucleotides based on peptide sequence are Sequence ID Nos. 6, 7, 8 and 9. The oligonucleotide primer is the complement to the DNA sequence which codes for the protein Sequence ID No. 10 derived from the leech antiplatelet protein. PCR reactions were performed as described in Innis, M. A., et al., PCR Protocols: A Guide to Methods and Applications, Academic Press, San Diego, Calif. 1990. The PCR product of these two oligos was a DNA fragment of about 500 base pairs when electrophoresed on agarose gel. This product was sequenced by standard methods and confirmed to code for both the oligonucleotide based peptide sequence and peptide sequence flanking the oligonucleotide primer.

This PCR product was radiolabeled using standard protocols and was then used to screen the lambda library, by hybridization, for the cDNA clones encoding entire gene. Ten plaque-pure clones were initially isolated. DNA was isolated from the lambda clones according to Maniatis, T. et al., Molecular Cloning: A Laboratory Manual, Cold Spring Harbor Laboratory, Cold Spring Harbor, N.Y. 1982. This DNA was digested with the restriction endonucleases NotI and SalI and the DNA electrophoresed in an agarose gel. A band of about 700 bp was cut out of the gel and electroeluted. An *E. coli* plasmid (Bluescript SK, Stratagene, LaJolla, Calif.) was cut with the restriction endonucleases NotI and SalI (FIG. 2) and the 700 bp fragment from the lambda clone subcloned into this vector. The subcloned fragment was then sequenced using standard techniques.

The LAPP mRNA has one long open reading frame followed by the polyA site and polyA tail. Computer translation of the open reading frame showed a protein of 147 amino acids. Within this sequence is found the five peptide sequences identified by protein sequencing. A leader peptide sequence of about 21 hydrophobic amino acids was also found. Computer analysis predicted that a peptidase cleavage site was between residue 21 and 22 giving a mature protein of 125 amino acids starting with Gln at residue 22.

The 147 amino acid sequence and corresponding DNA clone is shown in Sequence Id No. 1 and Sequence Id No. 2, respectively. The 125 amino acid sequence and corresponding DNA clone is shown in Sequence Id No. 3 and Sequence Id No. 4, respectively.

The predicted mature protein was then expressed in yeast using a Kex cleavage site in the expression vector pKH4α2. The mature gene was isolated by PCR generating a DNA fragment using the subcloned 700 bp fragment in the Bluescript vector as a substrate and the oligonucleotide primers Sequence ID Nos. 11 and 12.

The polymerase chain reaction resulted in a blunt end fragment which was regenerated in the usual fashion by digestion with BamHI. The correct fragment which obtained after electrophoresis on a 1% agarose gel, excision of the band and electroelution. The purified fragment was ligated with the yeast expression vector pKH4α2 (Jacobson, M. A. et al., (1989) *Gene* 85: 513-518) that had been previously digested with BamHI and treated with calf alkaline phosphatase to form pKH4.α2 LAPP (FIG. 1), which generates the protein of the invention. The correct sequence of plasmid clones in the correct orientation was confirmed by DNA sequence analysis. Fusion products produced are proteolytically processed by the Lys-Arg-cleaving endopeptidase (KEX2) encoded by the KEX2 gene and products are secreted into culture medium. KEX2 cleaves on the C-terminal side of Lys-Arg residues.

FIG. 1 shows construction of the yeast plasmid expression vector pKH4.α2 LAPP, used for the expression of the r-LAPP synthetic gene sequence. Representations are:

▨: LAPP open reading frame
☐: α-mating factor gene sequences
—: 2μcircle sequences
∼: pBR322 sequences
■: leu2$^d$ gene sequences
▣: GAL 10 promoter sequence.

A region of the coding sequence is shown which corresponds to the seven amino acids connecting peptide linking the α-mating factor precursor at glycine 79 to LAPP. Also shown is the predicted cleavage site recognized by the KEX2 protease.

TRANSFORMATION OF *SACCHARMOMYCES CEREVISIAE* BJ1995

Diploid yeast strain *Saccharmomyces cerevisiae* BJ1995 (Gardell et al., *Arch. Biochem. Biophys.* vol. 278, No. 2, pp. 467-474 (1990)) was transformed with pKH4.α2 LAPP using standard protocols (Hinnen et al., (1978) *Proc. Natl. Acad. Sci. USA* 75: 1929-1933).

From plates containing yeast transformants, single colony isolates were obtained. These isolates were grown in 5× Leu⁻ selective media (5× Leu⁻), Jacobson, M. A., et al., Gene 85, 1989. Cultures were grown in a 2L Erlenmeyer flask for 16-18 hours at 28° C. using a rotary shaker at 300 rpm prior to its inoculation into 5×Leu⁻ media containing 4% (w/v) galactose to induce expression. After 24 hours, the resulting media containing LAPP was separated from the cells by pelleting the cells.

DEPOSIT

The transformed yeast strain (*Saccharomyces cerevisiae* pKH4-LAPP-BJ1995), deposited with the American Type Culture Collection, Rockville, MD, USA, is designated ATCC 74020. The deposit was made Sep. 27, 1990 under the provisions of the Budapest Treaty on the International Recognition of the Deposit of Microorganisms for the Purposes of Patent Procedure and the Regulations thereunder (Budapest Treaty). Maintenance of a viable culture is assured for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention rights granted under the authority of any government in accordance with its patent laws.

THERAPY

The proteinaceous substance of this invention, which blocks stimulation of platelet aggregation by collagen, forms pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminium; and organic primary, secondary and tertiary amines, as for example, trialkylamines, including triethylamine, procaine, dibenzylamine, 1-ethenamine; N,N'-dibenzylethylenediamine, dihydroabietylamine, N-(lower)alkylpiperidine, and any other suitable amine.

The antithrombotic blood concentration of the proteinaceous substance of this invention which blocks stimulation of platelet aggregation by collagen is about 100 nMolar (or 1.6 μg/ml).

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Although the proteinaceous substance of this invention may survive passage through the gut following oral administration, applicants prefer non-oral administration, for example, subcutaneous, intravenous, intramuscular or intraperitoneal; administration by depot injection; or by implant preparation.

For parenteral administration the proteinaceous substance of this invention may be administered as injectable dosages of a solution or suspension of the substance in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The proteinaceous substance of this invention can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

Seq. Id No. 1

```
    1               5              10              15
Met Asn Ser Phe Leu Phe Ser Leu Ala Cys Ser Leu Leu Val Ala 20              25              30
         Ile Pro Ala Ile Arg Ala Gln Asp Glu Asp Ala Gly Gly Ala Gly 35              40              45
         Asp Glu Thr Ser Glu Gly Glu Asp Thr Thr Gly Ser Asp Glu Thr 50              55              60
         Pro Ser Thr Gly Gly Gly Gly Asp Gly Gly Asn Glu Glu Thr Ile 65              70              75
         Thr Ala Gly Asn Gly Asp Cys Trp Ser Lys Arg Pro Gly Trp Lys 80              85              90
         Leu Pro Asp Asn Leu Leu Thr Lys Thr Glu Phe Thr Ser Val Asp
```

```
                        95              100              105
Glu Cys Arg Lys Met Cys Glu Glu Ser Ala Val Glu Pro Ser Cys 110              115              120
Tyr Ile Leu Gln Ile Asn Thr Glu Thr Asn Glu Cys Tyr Arg Asn 125              130              135
Asn Glu Gly Asp Val Thr Trp Ser Ser Leu Gln Tyr Asp Gln Pro 140              147
Asn Val Val Gln Trp His Leu His Ala Cys Ser Lys
```

Seq Id No. 2

```
ATGAACTCAT TCCTGTTCTC ACTCGCCTGC TCCTTTGCTGG TTGCCATCCC AGCTATCAGG   60
GCCCAGGATG AAGATGCCGG TGGTGCCGGA GATGAAACCA GTGAAGGCGA AGACACTACT  120
GGAAGTGATG AAACACCCTC AACAGGAGGA GGAGGCGATG GTGGAAATGA AGAAACCATA  180
ACTGCTGGCA ATGGAGATTG CTGGTCTAAA CGGCCTGGCT GGAAGCTGCC TGACAATCTG  240
TTGACGAAGA CTGAATTCAC CAGCGTCGAT GAATGCAGAA AGATGTGCGA AGAATCTGCC  300
GTGGAACCAT CCTGCTACAT TCTGCAAATC AACACAGAAA CCAACGAATG GTATAGAAAT  360
AACGAAGGTG ATGTCACGTG GTCAAGTTTA CAATATGATC AACCAAATGT TGTTCAATGG  420
CACCTTCACG CTTGTTCAAA A                                            441
```

Seq Id No. 3

```
  1                5              10              15
Gln Asp Glu Asp Ala Gly Gly Ala Gly Asp Glu Thr Ser Glu Gly 20              25              30
Glu Asp Thr Thr Gly Ser Asp Glu Thr Pro Ser Thr Gly Gly Gly 35              40              45
Gly Asp Gly Gly Asn Glu Glu Thr Ile Thr Ala Gly Asn Gly Asp 50              55              60
Cys Trp Ser Lys Arg Pro Gly Trp Lys Leu Pro Asp Asn Leu Leu 65              70              75
Thr Lys Thr Glu Phe Thr Ser Val Asp Glu Cys Arg Lys Met Cys 80              85              90
Glu Glu Ser Ala Val Glu Pro Ser Cys Tyr Ile Leu Gln Ile Asn 95              100             105
Thr Glu Thr Asn Glu Cys Tyr Arg Asn Asn Glu Gly Asp Val Thr 110             115             120
Trp Ser Ser Leu Gln Tyr Asp Gln Pro Asn Val Val Gln Trp His

126
Leu His Ala Cys Ser Lys
```

Seq Id No. 4

```
CAGGATGAAG ATGCCGGTGG TGCCGGAGAT GAAACCAGTG AAGGCGAAGA CACTACTGGA   60
AGTGATGAAA CACCCTCAAC AGGAGGAGGA GGCGATGGTG AAATGAAGA AACCATAACT  120
GCTGGCAATG GAGATTGCTG GTCTAAACGG CCTGGCTGGA AGCTGCCTGA CAATCTGTTG  180
ACGAAGACTG AATTCACCAG CGTCGATGAA TGCAGAAAGA TGTGCGAAGA ATCTGCCGTC  240
GAACCATCCT GCTACATTCT GCAAATCAAC ACAGAAACCA ACGAATGCTA TAGAAATAAC  300
GAAGGTGATG TCACGTGGTC AAGTTTACAA TATGATCAAC CAAATGTTGT TCAATGGCAC  360
CTTCACGCTT GTTCAAAA                                                378
```

Seq Id No. 5
5' ATTCGTCGAC AATACGACTC ACTA 3'                                    24

Seq Id No. 6
5' ACGTTAGGTT GGTCGTATTG 3'                                         20

Seq Id No. 7
5' ACGTTCGGTT GGTCGTATTG 3'                                                        20

Seq Id No. 8
5' ACATTGGGCT GATCATACTG 3'                                                        20

Seq Id No. 9

5' ACGTTTGGTT GGTCGTATTG 3'                                                        20

Seq Id No. 10
 1         5     7
Gln Tyr Asp Gln Pro Asn Val

Seq Id No. 11
5' ATATGGATCC TGTCTTTGGA TAAAAGACAG GATGAAGATG CCGGTGGT                            48

Seq Id No. 12
3' ATATCGGGAT CCTATTTTGA ACAAGCGTGA AGG                                            33

What is claimed is:

1. A protein having a molecular weight of about 16,000 and which inhibits collagen-stimulated platelet aggregation wherein the protein is derived from the salivary gland of the leech Haementeria officinalis and wherein the protein has an amino acid sequence of Sequence ID No. 1 or Sequence ID No. 3.

2. A process for the production of a protein derived from the salivary gland of the leech *Haementeria officinalis* which inhibits collagen-stimulated platelet aggregation, comprising the steps of:
   a) dissecting and removing the salivary gland tissue of the leech;
   b) homogenizing and solubilizing the tissue in an aqueous solution comprising a buffered salt having a suitable fixed pH to produce a homogenate;
   c) centrifuging the homogenate to produce supernatant protein suspension fractions;
   d) assaying the fractions and selecting a product fraction which inhibits collagen-stimulated platelet aggregation;
   e) placing the supernatant fraction in contact with an affinity column of heparin agarose equilibrated with HEPES buffer, pH 7.8 and 10 mM $CaCl_2$;
   f) separating fractions containing proteins which are not adsorbed on the column from fractions containing proteins which are adsorbed on the column; and
   g) selecting from the adsorbed fractions a protein which inhibits collagen-stimulated platelet aggregation, said protein having an amino acid sequence selected from the group consisting of Sequence ID No. 1 and Sequence ID No. 3.

3. The product of claim 2 wherein the product fraction is characterized by in vitro inhibition activity for collagen-stimulated platelet aggregation.

4. The product of claim 2 wherein the product fraction is characterized by in vitro blocking activity of platelet adhesion to collagen.

5. A method of treating a mammal for the prevention of collagen-stimulated platelet aggregation comprising administering to the mammal, in a therapeutically effective dose, a protein of claim 1.

6. A therapeutic composition for inhibiting collagen-stimulated platelet aggregation comprising an effective amount of a protein of claim 1.

7. A protein of claim 1 having the amino acid sequence of Sequence ID No. 1 thereof which inhibits collagen-stimulated platelet aggregation.

* * * * *